(12) United States Patent
Osypka

(10) Patent No.: US 9,463,316 B2
(45) Date of Patent: Oct. 11, 2016

(54) TEMPORARILY IMPLANTABLE ELECTRODE ASSEMBLY FOR THE STIMULATION AND INTRACARDIAC CARDIOVERSION/DEFIBRILLATION OF THE HEART FOLLOWING SURGERY

(71) Applicant: Peter Osypka, Grenzach-Wyhlen (DE)

(72) Inventor: Peter Osypka, Grenzach-Wyhlen (DE)

( * ) Notice: Subject to any disclaimer, the term of this patent is extended or adjusted under 35 U.S.C. 154(b) by 0 days.

(21) Appl. No.: 14/465,253

(22) Filed: Aug. 21, 2014

(65) Prior Publication Data
US 2015/0066125 A1 Mar. 5, 2015

(30) Foreign Application Priority Data
Sep. 4, 2013 (EP) .................................... 13004327

(51) Int. Cl.
| | |
|---|---|
| *A61N 1/05* | (2006.01) |
| *A61N 1/39* | (2006.01) |
| *A61N 1/04* | (2006.01) |
| *A61N 1/368* | (2006.01) |

(52) U.S. Cl.
CPC ............ *A61N 1/059* (2013.01); *A61N 1/0492* (2013.01); *A61N 1/0597* (2013.01); *A61N 1/3684* (2013.01); *A61N 1/3968* (2013.01)

(58) Field of Classification Search
CPC .......................... A61N 1/3968; A61N 1/0597
USPC .......................................... 607/13, 129–130
See application file for complete search history.

(56) References Cited

U.S. PATENT DOCUMENTS

| | | | |
|---|---|---|---|
| 4,030,509 A * | 6/1977 | Heilman et al. ................. | 607/17 |
| 4,633,880 A * | 1/1987 | Osypka et al. ............... | 600/374 |
| 5,674,251 A | 10/1997 | Combs et al. | |
| 6,324,435 B1 * | 11/2001 | Shchervinsky et al. ...... | 607/152 |
| 2006/0100683 A1 * | 5/2006 | Yacoubian ........... | A61N 1/0587 607/129 |
| 2007/0106359 A1 * | 5/2007 | Schaer et al. .................. | 607/129 |

(Continued)

FOREIGN PATENT DOCUMENTS

| | | |
|---|---|---|
| DE | 202010011244 U1 | 11/2010 |
| DE | 202010016681 U1 | 5/2011 |
| DE | 102011111649 A1 | 2/2013 |

OTHER PUBLICATIONS

Extended Search Report dated Jan. 7, 2014 in connection with corresponding EP Application No. 13004327.6.

*Primary Examiner* — Carl H Layno
*Assistant Examiner* — Jennifer Ghand
(74) *Attorney, Agent, or Firm* — Locke Lord LLP; Scott D. Wofsy; Daniel J. Fiorello

(57) ABSTRACT

An electrode assembly for temporary cardioversion/defibrillation and/or for temporary stimulation of the heart after open heart surgery consisting of two defibrillation electrodes with at least one indifferent pole each and an elastic section is disclosed. Each defibrillation electrode in the operating position is positioned on the right and left atrium. The defibrillation electrodes each distally comprise a fixation member and each end in a protective tube to protect the epicardium at a proximal end. The fixation members are elastic and enable reversible fastening of the defibrillation electrodes in the pericardium on the right and left side. The protective tubes are preferably fed together into a guide tube, where the guide tube is slidable along the longitudinal axis. The stimulation electrodes (different electrode poles) for stimulation of the atria are designed appropriately together with the defibrillation electrode in one piece.

9 Claims, 5 Drawing Sheets

(56) References Cited

U.S. PATENT DOCUMENTS

| | | | |
|---|---|---|---|
| 2008/0046061 A1* | 2/2008 | Yacoubian | 607/126 |
| 2009/0299447 A1* | 12/2009 | Jensen et al. | 607/130 |
| 2010/0042108 A1* | 2/2010 | Hibino | 606/129 |
| 2010/0312296 A1* | 12/2010 | Gray | 607/5 |
| 2013/0158613 A1 | 6/2013 | Osypka | |
| 2014/0194965 A1 | 7/2014 | Osypka | |

* cited by examiner

TEMPORARILY IMPLANTABLE ELECTRODE ASSEMBLY FOR THE STIMULATION AND INTRACARDIAC CARDIOVERSION/DEFIBRILLATION OF THE HEART FOLLOWING SURGERY

The invention relates to a temporarily implantable elastic electrode assembly used for monitoring and/or stimulation of the heart and/or for cardioversion/defibrillation in case of postoperative atrial fibrillation. Thanks to its elasticity the electrode assembly is easily positioned on and fastened to the back-side of the heart without injuring the epicardium. At the end of the treatment the electrode assembly is easy to remove.

Temporary myocardial electrodes (also known as heart wires) allow external stimulation of the heart following heart surgery. Electrodes of this kind have been well-known for many years and are used routinely after any open heart surgery to stimulate the atria and ventricles. The anchorage of the heart wires and thus the stimulation of the heart's atria, especially stimulation of the left atrium, poses considerable problems due to the specific anatomical position of the left atrium. In open heart surgery only the left atrial appendage is visible, which is unsuitable for fastening heart wires due to its fragile tissue structure. The left atrium is located at the back side of the heart and is difficult to access in order to fasten a temporary electrode. Therefore, despite its major medical importance for prophylaxis and treatment of atrial fibrillation, stimulation of the left atrium is often dispensed with.

There is still a need to provide an electrode assembly that can be placed on the back-side of the heart around the left and right atriums, which is easy to fasten and which maintains its position on the atria in the usage position. The electrode assembly should allow an easy and quick stimulation, cardioversion/defibrillation of the heart's atria either separately or together. After completing the therapy the electrode assembly must be easily removable without injuring of the epicardium.

The inventive electrode assembly allows to be well positioned around the left atrium/atria and is on the other hand easily removable due to its specifically coordinated combination of an elastic defibrillation electrode with an elastic fixation member.

The invention therefore relates to an electrode assembly (1) for temporary cardioversion/defibrillation and/or for temporary stimulation of the heart after open heart surgery consisting of:
a) A first defibrillation electrode (11) with at least one indifferent pole (17) and an elastic section (13), where the defibrillation electrode (11) is positioned on the left atrium (3) in the usage position, said defibrillation electrode (11) comprises a fixation member (21) disposed on its distal end and proximally ends into a protective tube (6);
b) A second defibrillation electrode (10) with at least one indifferent pole (16) and an elastic section (12), where the defibrillation electrode (10) is positioned on the right atrium (2) in the usage position, said defibrillation electrode (10) comprises a fixation member (20) disposed on its distal end and proximally ends into a protective tube (5);
c) The different poles (18), (19);
whereby the fixation members (20) and (21) are fixed on the right and left side in the pericardium (4) when in use or are anchored to each other at the front of the heart and where the protective tubes (5) and (6) are optionally inserted together into a guide tube (7) whereby the guide tube is slidable along its longitudinal axis.

The electrode assembly allows stimulation as well as cardioversion/defibrillation between the pole pairs (16), (18) and (17), (19). In addition, it is also possible to cardiovert both atria of the heart between the indifferent poles (16), (17) at the same time.

The protective tubes (5), (6) are used to protect the epicardium. In the protective tubes (5), (6) the electric leads run to the poles of the electrodes. The leads are preferably flexible stranded wire.

If desired, additional stimulation electrodes may be present to stimulate the left and/or right atrium as well as to stimulate the ventricle. An additional bipolar stimulation electrode to stimulate the left atrium is shown in FIG. 2. The electrical lead for the stimulation electrode is also fed as required through the guide tube (7).

FIG. 9 shows stimulation electrodes for the ventricle.

In a preferred embodiment the guide tube (7) is present. The advantage of the guide tube is that after fastening the defibrillation electrodes it is possible to adjust the position of the electrode poles by simply shifting the guide tube.

The guide tube is made of plastic, polyethylene, for example. It forms a channel for the protective tubes (5) and (6) and is slidable in a longitudinal direction. At the top end of the guide tube (7) the protective tubes (5) and (6) protrude. The electrode poles are connected to the electrical leads that run through the protective tubes. At the bottom end the protective tubes are fed outside through an opening in the chest and the electrical leads are connected to a pacemaker or defibrillator.

If the guide tube is moved upwards the protective tubes (5), (6) move closer together. This reduces the distance between the electrode poles. If the guide tube is pulled down the distance between the electrode poles is increased. As such, any electrode assembly can be easily adapted to the anatomical conditions of any particular heart.

The defibrillation electrode is connected to the electrical lead proximally and supports the fixation member distally.

In one embodiment the defibrillation electrode is made of an insulated stranded wire and a pole wire. The pole wire represents the indifferent electrode pole. The pole wire is made of a conductive metallic material, preferably a shape memory material such as nitinol.

The pole wire may be reinforced by sliding open at least one coil. Several coils can also be slid open. The coil is made of an electrically conductive material, preferably platinum or stainless steel and it reinforces the pole wire and thus improves contact with the heart surface.

The different electrode pole (stimulation electrode) may be attached to the defibrillation electrode. The different electrode pole is formed, for example, as an insulated clamping sleeve, which is arranged on the pole wire and is isolated against the pole wire or the different electrode is part of the pole wire.

The pole wire can be insulated on the side turned away from the heart by a coating of plastic. This method avoids a current flow into the pain-sensitive sides facing away from the heart.

The defibrillation pole may also consist of a stainless steel stranded wire. The different electrode pole is formed as an insulated clamping sleeve, for example, which is arranged on the strand and is isolated against the stranded wire or the different electrode is part of the strand. The strand can also be insulated on the site turned away from the heart by a coating of plastic.

In one embodiment the surface of the metallic poles is covered with a coating of platinum or gold. Covering the electrode pole with a precious metal coating is especially important in order to prevent the formation of an oxide layer as the result of cardioversions.

In one embodiment the defibrillation electrode is in a tubular shape. The tube is made of a flexible material. Suitable materials are, for example, silicone, dacron, polyurethane, polyester, silk or polyamide. The tube consists of at least a lumen to receive the electrodes. On the side facing towards the heart the tube has several openings for the indifferent pole and one opening for the different pole, said openings allowing an electrical current flow during stimulation/cardioversion. A current flow into the pain-sensitive sides facing away from the heart is avoided as the tube as no openings on the side facing away from the heart.

In the above tubular shaped assembly the two poles of the defibrillation electrodes consist of a coil of, for example, six insulated wires of stainless steel, which coil is integrated in the tube with the appropriate openings. Inside the coil there is a low impedance lead, for example a lead made of silver or a precious metal, which is electrically connected to the coil distally. At the appropriate openings of the tube the insulation is removed from four coil wires, so that an electric current can flow through the wires arrayed in parallel. The coil's two remaining insulated wires form proximally the different electrode pole after removal of the insulation at the appropriate opening. By applying a precious metal using laser technology to the poles in the openings (bumps), the electrical properties of the poles can be improved with regard to oxide coating formation.

Elastic Section

The elasticity of the defibrillation electrode is essential, which is caused by what is referred to as an elastic section. The elastic section describes an area on the defibrillation electrode, which can be pulled apart and which after the defibrillation electrode is fastened contracts to its original shape again.

This can be achieved, for example, by forming a wave shaped defibrillation electrode or a defibrillation electrode in shape of a circle, an ellipsis, a polygon (Hexagon) or any other shape, which can be pulled apart. An especially suitable material for shaping is a shape memory material such as nitinol. The elastic section is thus wave shaped or in shape of a circle, an ellipsis or a hexagon. But it is also conceivable that the defibrillation electrode or parts of it are made of a stretchable plastic such as silicone to which the electrode poles are attached.

The elastic section allows the defibrillation electrode to be pulled apart when placing the electrode assembly around the atria on the back side of the heart, which makes it easier to push up the electrode assembly under the heart. The elastic section simultaneously enables the fixation of the defibrillation electrode by drawing the fixation member through the pericardium. Once the fixation members have been positioned, the defibrillation electrode adopts its original shape again and thus provides an optimal contact of the electrode poles on the heart surface. When the defibrillation electrode contracts into its original shape an anchorage in the pericardium is achieved at the same time. Furthermore, the elastic section is flexible in design and shape. This flexibility allows to circumvent bypasses or wounds incurred in surgery.

Fixation Member

For fastening purposes the defibrillation electrode has a fixation member at the distal end facing the pericardium. The fixation member has to fulfil two functions. Firstly, a firm anchorage of the defibrillation electrode during the treatment period, while on the other hand the anchor should be easily removable once the treatment is completed. The removal is carried out through a small opening, while the thorax is otherwise closed.

Suitable fixation members for fastening in the pericardium are all those known state of the art members such as zigzag, anchor, eyelets, loop, coil, V-shape, elastic T-bar, knot.

The fixation members (20) and (21) may be the same or different. In a preferred embodiment they are the same, which means both the fixation member (20) as well as the fixation member (21) are anchors, for example.

The fixation members are drawn through the pericardium with a heart needle, for example. Once fastened, the heart needle is cut off. The positioning and fastening can also be carried out with the aid of an insertion set.

As the anatomical size of the heart can vary greatly, the distance between the pericardium and the atria is important. The correct distance can be achieved by designing the fixation members (e.g. anchor or zigzag) at such a length that they can be fixed at any of the electrode poles' desired position.

In one embodiment the fixation member is an anchor, for example. The anchorage is achieved by splaying the anchor. With the heart needle the defibrillation electrode is drawn through the pericardium until the desired anchor has come out. By drawing back the defibrillation electrode the anchor splays out. The rest is cut off.

In one embodiment fixation is intended on the front side of the heart. Both defibrillation electrodes are drawn around the atria of the heart and the two fixation members are temporarily connected at the front side of the heart. In this embodiment the fixation members consist appropriately of two interlocking plates, which are put together and fastened using a thread. The thread is fed outwards like the electrical leads of the electrode assembly through a small opening in the human's body. After use the thread can be pulled and the fastening elements separate, so the electrode assembly can also be removed from the back side of the heart through the front opening.

It is structurally advantageous if the sections in the front area of the heart are insulated and also formed into undulating sections. As presented above, a firm fit of the electrode assembly on the heart is achieved by the elastic properties of the defibrillation electrode.

The inventive electrode arrangement allows not only optimum cardioversion/defibrillation and stimulation of the heart's atria but in addition simultaneous stimulation of the ventricles. As such, bipolar stimulation electrodes are attached at suitable points on the electrode assembly in the front and back sections of the heart.

The major benefit of the inventive electrode assembly is that due to the construction of the electrode assembly the surgeon is able to position and fasten the defibrillation electrodes on the left and right atrium and after fastening them is able to adjust them if necessary by simply pushing the guide tube. Thus an excellent contact is achieved between the electrode and the heart surface without injuring the epicardium. The electrode contact is optimised in such a way that defibrillation can be performed at extremely low shock energy levels. An extremely low shock energy level is in the range of 0.1 joules or less.

DRAWINGS

Further details, features and benefits of the invention can be found in the following descriptive section, in which the invention is described in more detail using drawings and version examples. The drawings show the following in schematic presentation.

FIG. 1 An example of an electrode assembly with an undulating elastic section placed over the left and right atrium on the back side of the heart and anchored in the pericardium.

FIG. 2 An example of an electrode assembly with an undulating elastic section placed over the left and right atrium on the back side of the heart and anchored in the pericardium. Possible fixation members are shown. An additional stimulation electrode for the left atrium is present.

FIG. 3 An example of an electrode assembly with a hexagonal elastic section placed over the left and right atrium on the back side of the heart and anchored in the pericardium.

FIG. 4 An example of an electrode assembly with a circular elastic section placed over the left and right atrium on the back side of the heart and anchored in the pericardium.

FIG. 5 An example of an electrode assembly with an elastic section connecting both the defibrillation electrodes.

FIG. 6 An example of an electrode assembly with an undulating elastic section and a defibrillation electrode in tubular form.

FIG. 7 An example of an electrode assembly with an undulating elastic section and a defibrillation electrode in tubular form. The tubular sections are dendritic.

FIG. 8 An example of an electrode assembly with an undulating elastic section and a defibrillation electrode in tubular form.

FIG. 9 An example of an electrode assembly with an undulating elastic section. The fixation members are anchored on the front side of the heart. Additional stimulation electrodes for stimulation of the ventricles are present.

FIG. 10 An example of an electrode assembly with divided hexagonal elastic sections placed over the left and right atrium on the back side of the heart and anchored in the pericardium.

Figure 1:
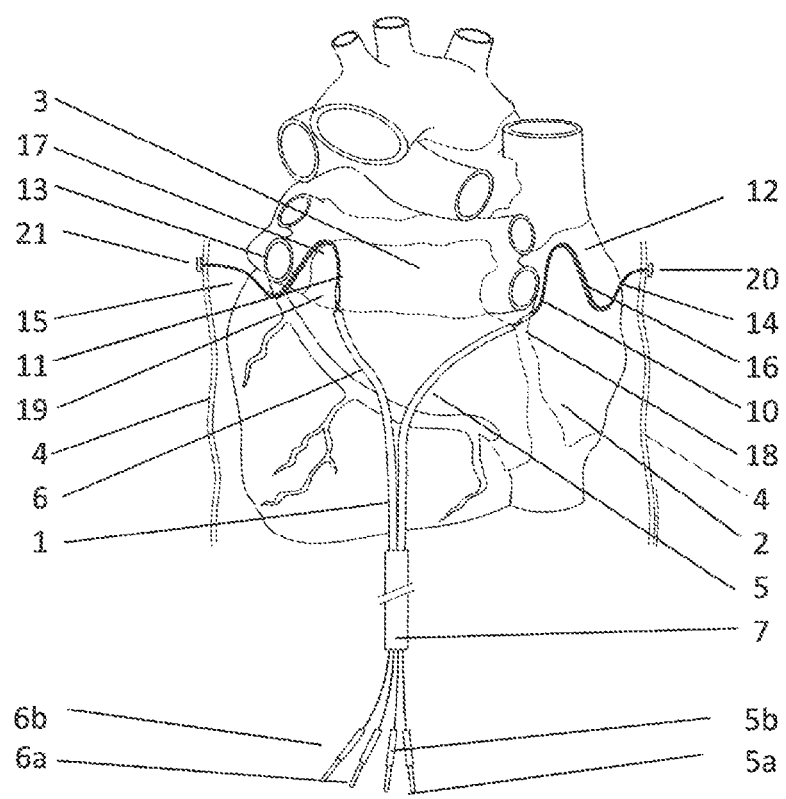
FIG. 1 shows the back area of the heart with the electrode assembly fastened in the pericardium. The electrode assembly (1) consists of two defibrillation electrodes (10) and (11). The indifferent poles (16) and (17) are pole wires. Defibrillation electrode (10) is positioned on the right atrium (2). Defibrillation electrode (11) is positioned on the left atrium (3). The pole wires are made of nitinol wire, which has been given an undulating shape by annealing, so that the pole wires each have one elastic section (12) and (13). The elastic sections (12), (13) are wave shaped consisting of a crest and a trough. Each pole wire leads into an electrically insulated stainless steel stranded wire (14) and (15), which leads distally to the fixation member (20) and (21). The fixation member is an elastic T-bar made of silicone, for example, which is anchored in the pericardium (4). The pole wires (16) and (17) are reinforced by inserted coils.

The two mutually insulated leads (5a) and (5b) or (6a) and (6b) are fed together in a protective tube (5) and (6) to the different electrode pole (18) or (19), which is designed as a clamping sleeve. Lead (5a) is electrically conductively connected with the inside of the clamping sleeve (18). Lead (5b) leads to the indifferent pole wire (10). Lead (6a) is electrically conductively connected with the inside of the clamping sleeve (19). Lead (6b) leads to the indifferent pole wire (11).

Protective tubes (5) and (6) are fed together into the guide tube (7). Guide tube (7) is slidable along its longitudinal axis, so that the distance between the two defibrillation electrodes (10) and (11) and between the two different electrode poles (18) and (19) is variable. If the guide tube (7) is pushed upwards the two clamping sleeves (18) and (19) come closer together. Also the shape and spacing of the defibrillation electrodes (10) and (11) change.

Figure 2:
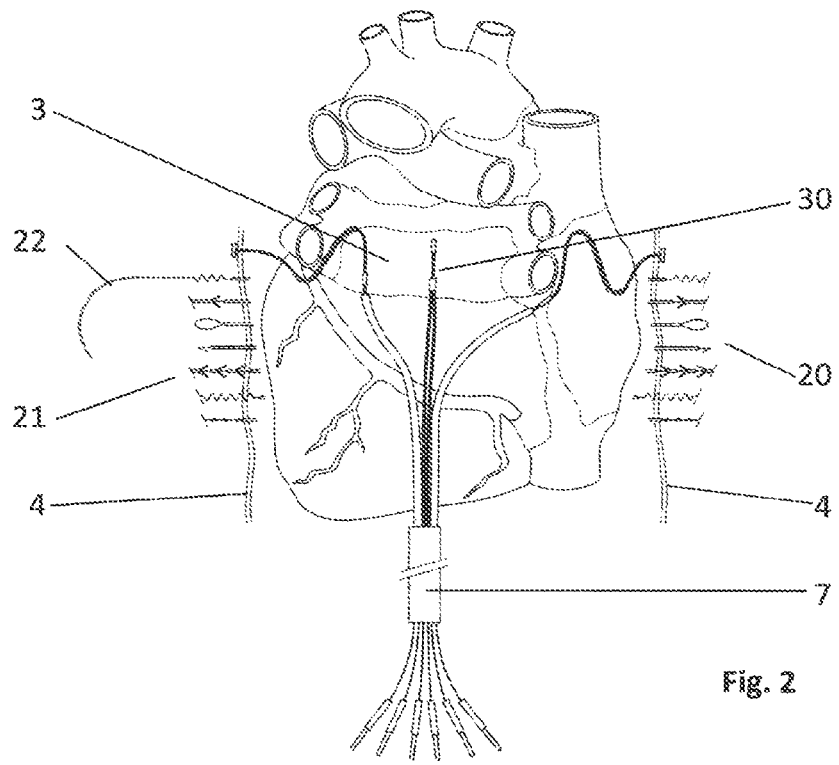

FIG. 2 shows the electrode array presented in FIG. 1. The fixation member (20) and (21) may take on various forms such as a zigzag, anchor, loop and hook, knot, multiple anchors, multiple knots. With the heart needle (22) the pole wire is pulled through the pericardium (4) until the fixation member has passed through; if the fastening element is a multiple anchor until the desired anchor has passed through. By pulling back the pole wire the fastening element is anchored in the pericardium.

In the version shown in FIG. 2 the electrode array has a second bipolar stimulation electrode (30), whose electric leads are also fed through the guide tube (7). The stimulation electrode (30) allows further stimulation of the left atrium (3).

Figure 3:
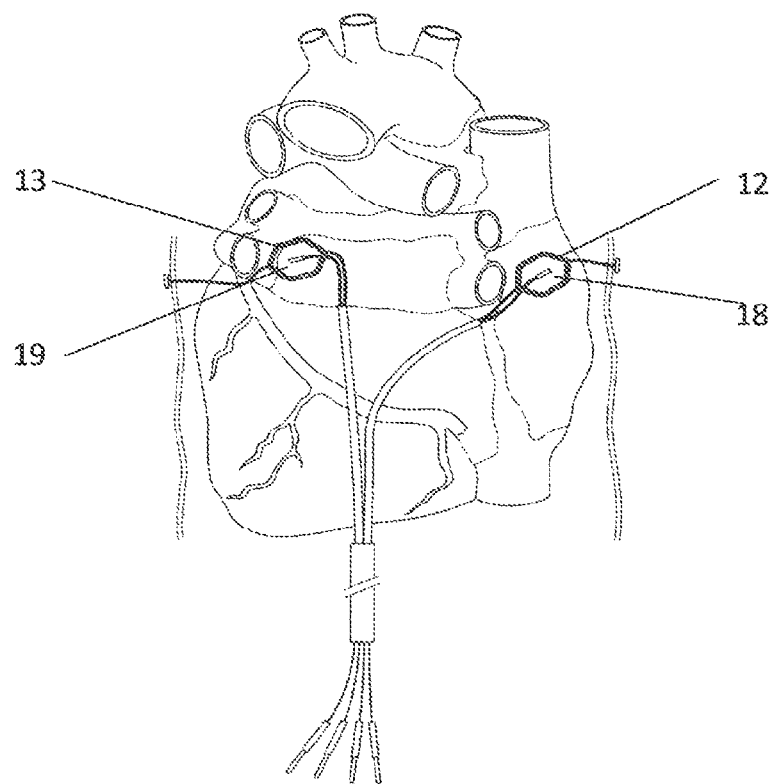

FIG. 3 shows the electrode array presented in FIG. 1, where the elastic sections (12) and (13) have a hexagonal shape. The pole wires of the indifferent poles are reinforced in the hexagonal zone by coils. The different electrode poles (18) and (19) lie within the hexagon.

Figure 4:
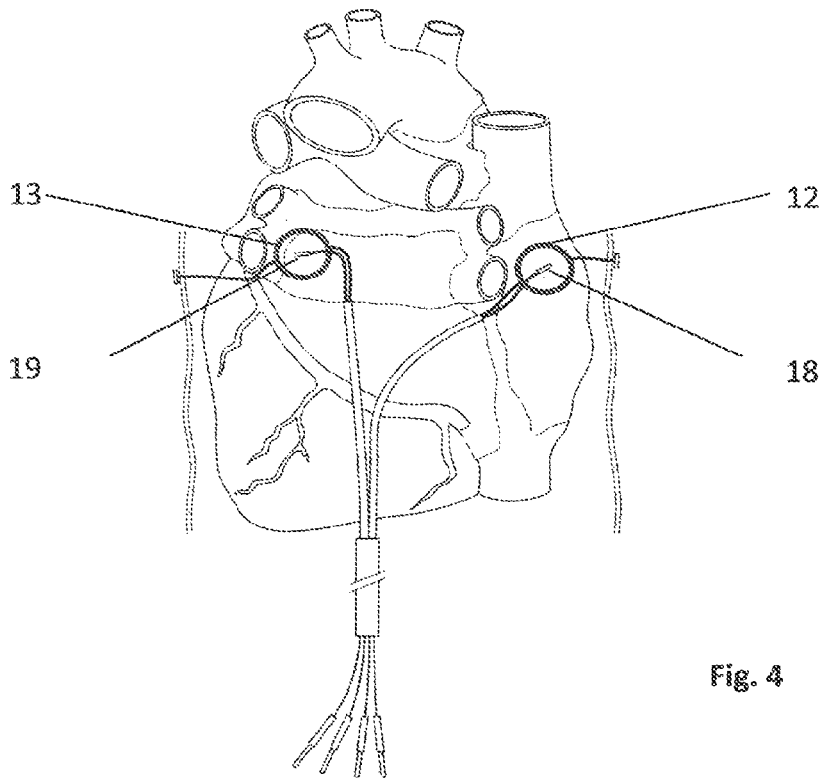

FIG. 4 shows the electrode array presented in FIG. 1, where the elastic sections (12) and (13) have a circular shape. The pole wires of the indifferent poles are reinforced in the circular zone by coils. The different electrode poles (18) and (19) lie within the circle.

Figure 5:
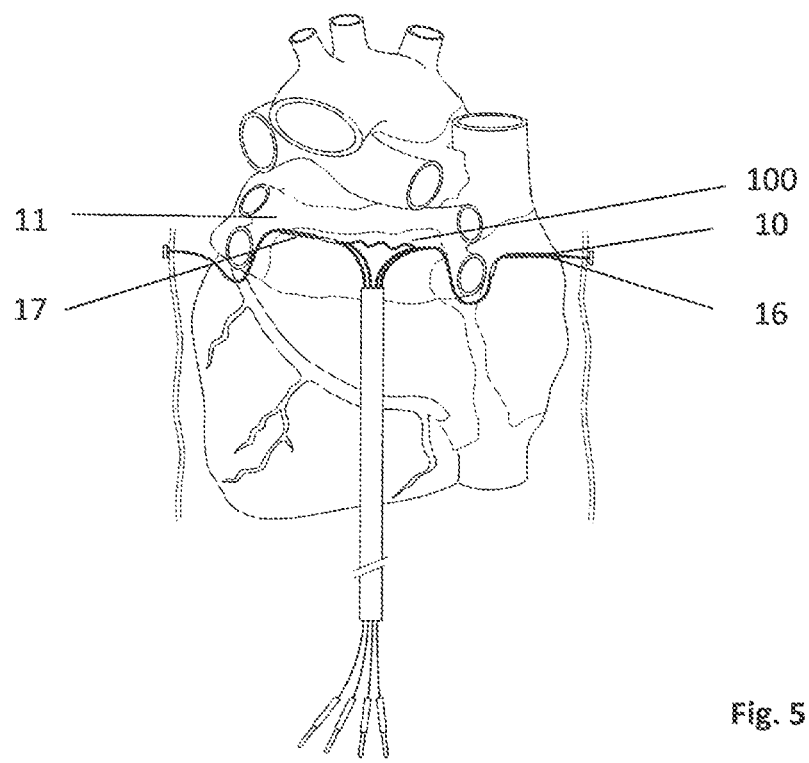

FIG. 5 shows the electrode array presented in FIG. 1, which is characterised by a special arrangement of the elastic section. The defibrillation electrodes (10) and (11) with pushed-up coils (16) and (17) are connected by the elastic section (100). The elastic section consists of an undulating-shaped insulated thread or a stretchable silicone thread, for example, which is fastened to both the defibrillation electrode (10) as well as defibrillation electrode (11).

Figure 6:
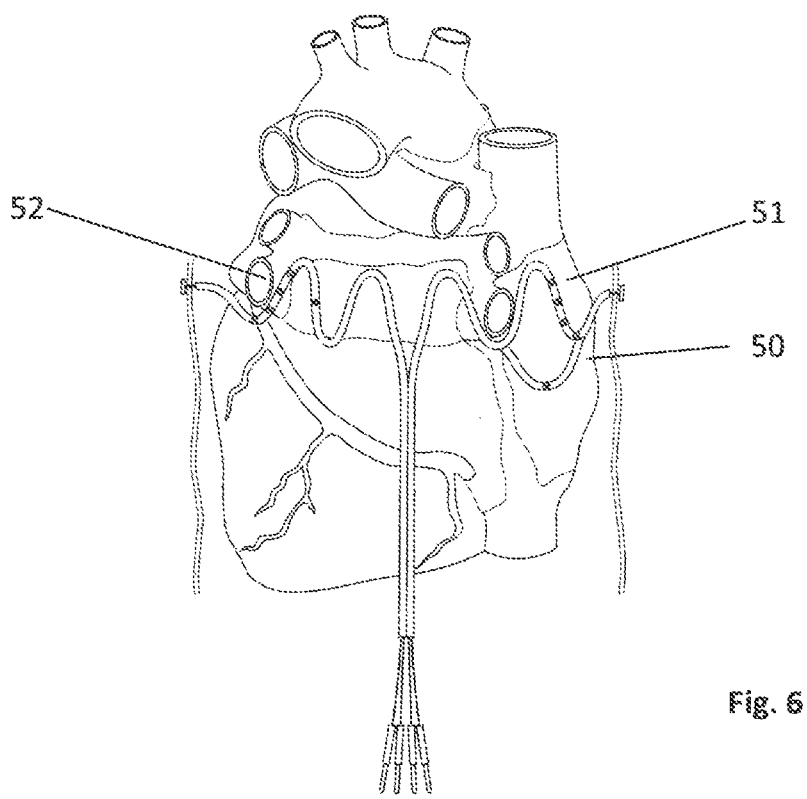

FIG. 6 shows the electrode array presented in FIG. 1, which is characterised by a special arrangement of the defibrillation electrode in protective tubular form over the left and right atrium on the back side of the heart. Above the right atrium there are two protective tube sections (50) with several openings for the indifferent pole (51) and with an opening for the different poles. The two protective tubular sections are shaped in such a way that the openings always face the heart when the electrode array is positioned and a current flow into the pain-sensitive parts facing away from the heart is avoided when giving the shock. The openings of the undulating protective tubular section (52) over the left atrium fulfil the same purpose.

Figure 7:
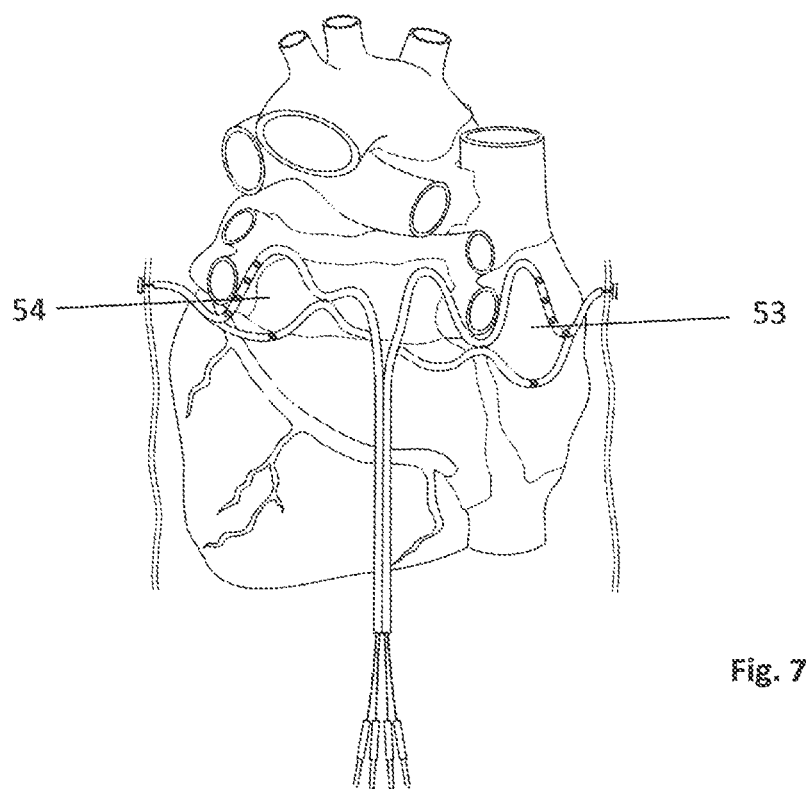

FIG. 7 shows another example of an electrode assembly with an undulating elastic section and a defibrillation electrode in protective tubular form over the left and right atrium on the back side of the heart. The protective tubular sections (53), (54) are shaped in such a way that the unintentional twisting of the openings while positioning them is prevented.

Figure 8:
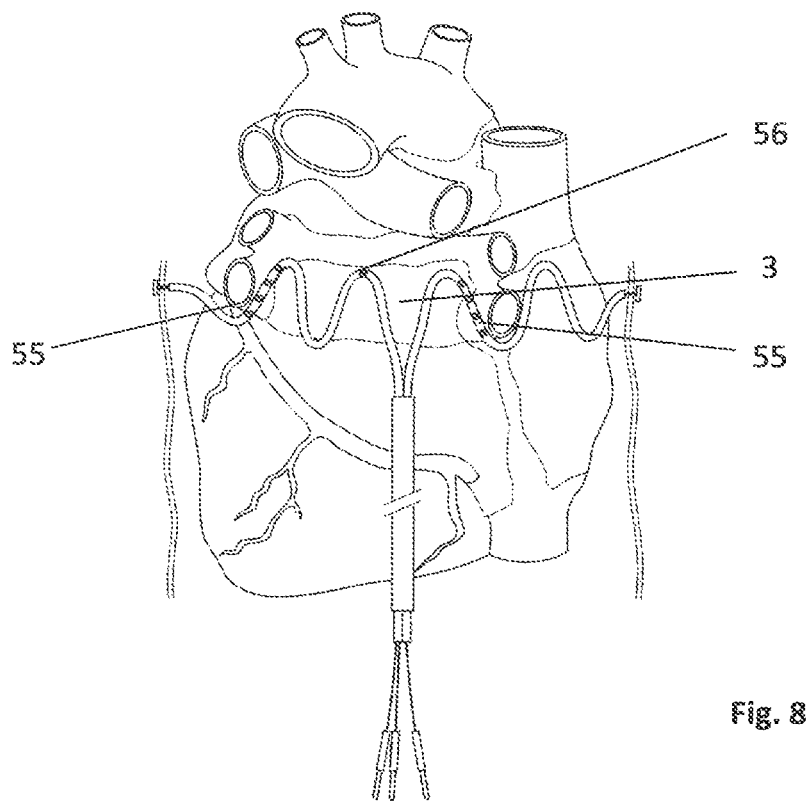

FIG. 8 shows another example of an electrode assembly with an undulating elastic section, in which only the left atrium (3) can be cardioverted/stimulated. With a separate electrode assembly (not shown) on the back side of the heart or on the front side of the heart the right atrium can also be cardioverted/stimulated. The elastic protective tubular shaped electrode assembly above the left atrium has two separate indifferent poles (55) and a different pole (56). Between the different pole (56) and the indifferent poles (55) the left atrium can be stimulated and cardioverted. This means the shock energy required for cardioversion can be reduced to a minimum, which is an advantage for patients in terms of pain sensitivity.

Figure 9:
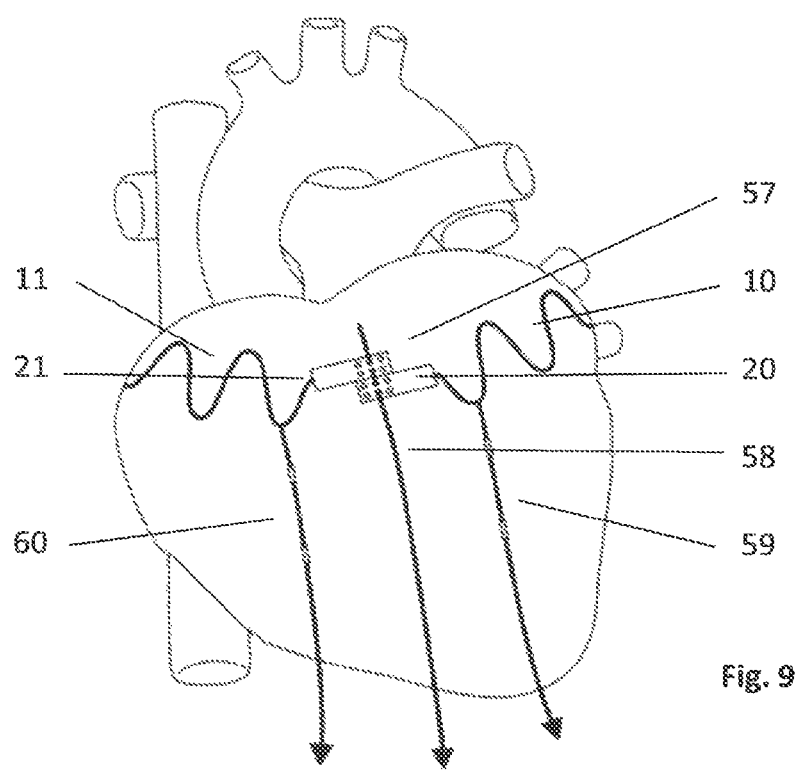

FIG. 9 shows the front of the heart. The defibrillation electrodes (10) and (11) support the fixation members (20) and (21), which are assembled from two interlocking plates (57), which are held together by means of a thread (58). After use the thread can be pulled and the fixation elements separate, so that the electrode assembly can also be removed from the back side of the heart through the front opening. The defibrillation electrodes (10) and (11) are fed wave-shaped over the front area of the heart up to the interlocking plates. In the front area of the heart above the ventricles additional separate bipolar electrodes (59), (60) are attached, whose purpose is to stimulate the right and left ventricle.

Figure 10:
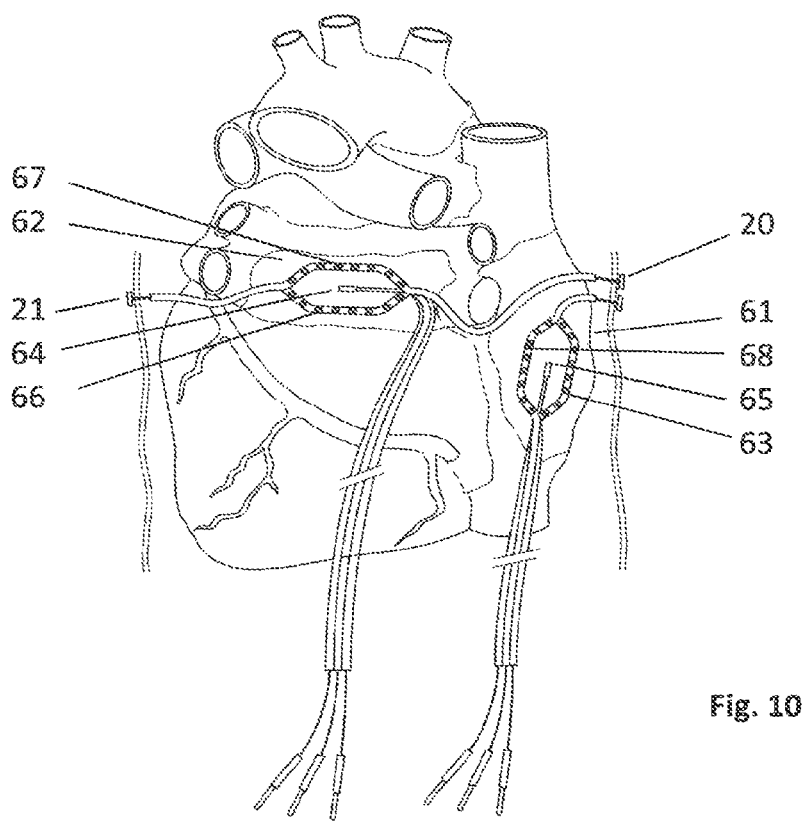

FIG. 10 shows another version of the invention's electrode assembly, where the elastic sections have a hexagonal shape (61), (62). The hexagonal indifferent electrode (62) that covers the entire left atrium is fastened separately to both sides of the pericardium (20), (21). The hexagonal indifferent electrode (61) that is placed over the right atrium is placed on one side of the pericardium in such a way that the placement meets the requirement of the particular anatomical shape of the right atrium. Stimulation takes place between each of the different poles (63), (64) within the hexagon and the elongated external sections (65), (66) of the hexagon. Cardioversion takes place separately in the left and right atrium respectively. In the left atrium cardioversion takes place between the electrically separate poles of the upper (67) and lower (66) part of the hexagon. In the right atrium cardioversion takes place between the electrically separate poles of the right (65) and left (68) pole of the hexagon.

The invention claimed is:

1. Electrode assembly for temporary cardioversion/defibrillation and/or temporary stimulation of the heart after open heart surgery comprising:
    a first defibrillation electrode with at least one indifferent pole and an elastic section, where the first defibrillation electrode is adapted to be positioned on the left atrium in the usage position, said first defibrillation electrode includes a fixation member disposed on its distal end and proximally ends into a protective tube;
    a second defibrillation electrode with at least one indifferent pole and an elastic section, where the second defibrillation electrode is adapted to be positioned on the right atrium in the usage position, wherein said second defibrillation electrode includes a fixation member disposed on its distal end and proximally ends into a protective tube;
    a pair of different poles; and
    a guide tube, whereby the fixation members are adapted to be fixed on the right and left side in the pericardium when in use or are adapted to be anchored to each other at the front of the heart and wherein the protective tubes of the first and second defibrillation electrodes are both inserted into the guide tube that is slidable along its longitudinal axis such that after fastening the first and second defibrillation electrode, wherein the guide tube is slidable along its longitudinal axis such that after fastening the first and second defibrillation electrode, the distance between the first and second defibrillation electrode and between the different poles is adjustable by shifting the guide tube along its longitudinal axis.

2. The electrode assembly according to claim 1, wherein the indifferent poles are pole wires.

3. The electrode assembly according to claim 2, wherein the pole wires are made of nitinol.

4. The electrode assembly according to claim 1, wherein the indifferent poles are formed from stranded wire.

5. The electrode assembly according to claim 1, wherein the surface of the indifferent poles are coated with a layer of platinum or gold.

6. The electrode assembly according to claim 1, wherein the first or second defibrillation electrode is a tube with at least one lumen to receive one or more electrodes and with several openings for the indifferent pole and one opening for the different pole.

7. The electrode assembly according to claim 1, wherein the different poles are configured as clamping sleeves.

8. The electrode assembly according to claim 1, wherein the elastic sections are present in wave form, circular form, elliptical form or a polygon.

9. The electrode assembly according to claim 1, wherein the fixation members are selected from the group consisting of a zigzag element, an anchor, an eyelet, a loop, coil, a V-shaped element, an elastic T-bar, or a knot.

* * * * *